(12) United States Patent
Rivera et al.

(10) Patent No.: US 6,341,153 B1
(45) Date of Patent: Jan. 22, 2002

(54) SYSTEM AND METHOD FOR PORTABLE NONDESTRUCTIVE EXAMINATION WITH REALTIME THREE-DIMENSIONAL TOMOGRAPHY

(75) Inventors: Charles Rivera, Annapolis; Robert A. Rashford, Darnascus, both of MD (US)

(73) Assignee: Genesis Engineering Company, Lanham, MD (US)

( * ) Notice: Subject to any disclaimer, the term of this patent is extended or adjusted under 35 U.S.C. 154(b) by 0 days.

(21) Appl. No.: 09/698,463

(22) Filed: Oct. 27, 2000

(51) Int. Cl.[7] .............................................. G01N 23/083
(52) U.S. Cl. ................ 378/4; 378/10; 378/19; 378/901
(58) Field of Search ........................... 378/4, 8, 10, 17, 378/19, 901

(56) References Cited

U.S. PATENT DOCUMENTS 5,172,695 A * 12/1992 Cann et al. ................. 600/407

* cited by examiner

Primary Examiner—David V. Bruce
(74) Attorney, Agent, or Firm—Roberts Abokhair & Mardula, LLC

(57) ABSTRACT

A system and method for non-destructive examination of parts using three-dimensional CT imagery. The system comprises a computer controlled x-ray source, a scintillator screen, and an amorphous silicon sensor array, which electronically records and transmits a series of images taken from different angles back to the computer system having a CAD/CAM software program. The part being examined is stored as a CAD/CAM record. The various images from the silicon sensor array are stored in the computer system and reconstructed as a three-dimensional CT image. That CT image is converted to the CAD/CAM coordinate space so a comparison between the CT image and the stored drawing of the part being examined may be made to detect any defects in the part. The overlaid or superimposed images are displayed for an analyst so that determination of a defect and a location can be made.

4 Claims, 1 Drawing Sheet

SYSTEM AND METHOD FOR PORTABLE NONDESTRUCTIVE EXAMINATION WITH REALTIME THREE-DIMENSIONAL TOMOGRAPHY

FIELD OF THE INVENTION

This invention relates to non-destructive examination (NDE) of objects. More particularly the present invention is a system and method for nondestructive examination using portable computer aided tomography (CT) system.

BACKGROUND OF THE INVENTION

Non-destructive examination of objects is a key aspect of present day engineering and development. Such items as aircraft engines, rocket motors, industrial robots, and a host of other construction and industrial pieces of equipment all require critical inspection. It is extremely important to know the status and structural integrity of elements before they are assembled into a finished product in order to insure safety stability, and usefulness of the finished object. Further, with increasing complexity to complete comes as an increasing expense. Thus destructive testing in order to find flaws in manufacturing can be an extremely expensive operation. Non-destructive testing and examination provides an appealing alternative and one, which leaves the structural integrity of the object being tested intact.

Different types of non-destructive examination (NDE) include liquid dye penetration, magnafleuxing and ultrasonic inspection, inferred imaging, and x-ray radiographs, all of which are alternatives used to examine the internal structure of objects.

X-ray examination generally provides a planar photograph recorded on film. Interpretation of the x-ray film requires special training in order to provide a proper diagnosis of the contents of the x-ray. Such x-rays represent a two-dimensional examination of the object. However, the ability to examine an object three-dimensionally improves visualization of internal phenomenon and simultaneously improves the diagnosis of examination of an object. When the object comprises a complex structure; a three-dimensional examination allows a more complete examination and diagnosis of the quality of an object.

Two-dimensional x-ray images can be used to create a three-dimensional visualization of objects. This technique, referred to as computerized-assisted tomography, or CAT scanning, provides very accurate positioning and information within three-dimensional space, capturing an object being examined. Such a three-dimensional image is created by utilizing multiple two-dimensional density maps, created by x-rays, to create a volumetric image of the object being examined.

Most CAT scan systems are large stationary systems, which typically do not operate in real time. Numerous two-dimensional x-rays must be obtained before the three-dimensional image can be created using mathematical algorithms known to those skilled in the art. In typical practice, several hundred projections are used in order to construct the three-dimensional image of the object under examination.

While such CT systems are a form of NDE, they are extremely expensive. Further, items that are to be inspected must be shipped to the facility having the CT system. Further in some cases objects are so large that the CT examination may not be possible.

The current scientific literature indicates that it is possible to use three x-ray images at different angles to reconstruct a three-dimensional image. This techniques is described in the paper entitle "Three-dimensional binary image reconstruction from three two-dimensional projections using a randomized ICM alba rhythm," Discrete Tomography Workshop, by F. Retraint, F. Peyrin, and J. M. Dinten, Aug. 1997 Hungary, John Wirely and Sons, Inc., Volume 9, pages 135–146 (1998) whose contents arc incorporated herein by reference in their entirety. This technique is based on using discrete tomography techniques to simplify the interpretation of the density patterns of the individual x-rays. The reduced number of x-rays required allows generation of three-dimensional images.

It would be truly useful to have a system and method for creating three-dimensional CT images for non-destructive examination in real time. Further, it would additionally be useful to compare such images to known engineering information about the object being examined in order to more precisely examine at pin point any defects in the object. Such a system would also be portable.

SUMMARY OF THE INVENTION

In view of the above discussion it is therefore an objective of the present invention to provide three-dimensional non-destructive examination.

It is a further objective of the present invention to utilize a system for three-dimensional NDE that is portable and can be brought to the work or launch site to create a three-dimensional image.

It is yet another objective of the present invention to create three-dimensional NDE images in near real time in order to assess the integrity of the object being examined.

It is still another objective of the present invention to use a priori information about the object being examined in order to assist in reconstruction of the three-dimensional image.

It is still another objective of the present invention to convert three-dimensional NDE images to CAD/CAM system images to allow for further manipulation.

It is a further objective of the present invention to compare three-dimensional NDE images to CAD/CAM drawings of the object being tested in order to precisely identify defects.

It is yet another objective of the present invention to create a true three-dimensional volumetric image of the object being tested in near real time.

It is still another objective of the present invention to use the volumetric image created to provide a cutaway view of the object so that both the density and position of elements can be analyzed.

It is a further objective of the present invention to utilize CAD/CAM system capabilities to allow the super position of actual three-dimensional failures onto the drawing of the part in question to promote more rapid analysis.

It is still another objective of the present invention to perform finite element analysis (FEA) to determine conditions, which cause any defect that is imaged.

It is a further objective of the present invention to allow for electronic comparison of one image to another to analyze simpler failures of parts.

The present invention comprises a three-dimensional computerized tomography system for analysis of engineering defects of parts. The system is a three-dimensional system comprising of a processor for receiving information from a plurality of x-rays and for reconstructing those x-rays into a three-dimensional image, and an imaging screen for creation of the image that is subsequently stored.

The portable NDE system of the present invention is a hand portable system that can be carried to a work site to perform the NDE discussed above. As noted above, the system comprises preferably but without limitation a laptop computer, a portable x-ray source, and an imaging means to recording the x-ray images.

The laptop computer, may be in a form of portable computational capability be it a laptop computer, small computer system, or special purpose handheld device. The computer receives the three-dimensional CT images and creates a three-dimensional image based upon the CT images required. The three-dimensional CT images are exported into a CAD/CAM system such as the Pro-Engineer system from the PCT, Inc., 128 Technology Drive, Waltham, Mass. 02453, whose capabilities are incorporated by reference herein in their entirety. The Pro-Engineer system allows the superposition of the actual three-dimensional image onto a drawing of the part that is stored in a Pro-Engineer coordinate system. Once the three-dimensional CT images are in the Pro-Engineer coordinate space, a module such as the Pro-Mechanica program is used to perform a finite element analysis (FEA) to determine conditions, which eventually cause the defect.

These images can be viewed by an engineer to perform the appropriate analysis for the part in question. Further, the Pro-Engineer software allows proper manipulation of the CT images against the stored drawings of the part in order to precisely locate any defects identified.

Utilizing the system of the present invention which one can conduct an inspection of electrical and mechanical components, perform failure analysis, do rapid prototype development, do current engineering of other parts relating to the product inspection, perform reverse engineering, and conduct research and development of new materials and processes.

The present invention allows non-destructive measurement and dimensioning of interior as well as exterior surfaces. Further, it does not require elaborate fixtures preprogramming as would be the case where large objects must be brought to a specific facility, secured, subsequently imaged. Further, the system of the present invention generates dense, well-behaved digital models without the discontinuities that are typically found using coordinate measuring machine (CMM) and laser data. It is unaffected by surface finish and or material composition and automatic only provides digital models with known topology, connectivity, and surface normals.

Using the system of the present invention one can simultaneously provide defect detection and quantification as well as location of the defects discovered. It also provides a methodology that is equal in speed to laser examination and (CMM). It will play an essential role in rapid prototyping, rapid tooling, and first article inspection.

The system comprises a portable computer having storage and processing capability. The satisfactory computers for the present invention are those comprising Pentium class processors with one other 128 megabytes of RAM and associated disk storage, operating on the windows, and windows NT operating system. Other computer systems having similar capabilities are also appropriate for this task. In order to obtain real time digital images a DPIX Flash Scan 30 imager is used instead of scanning x-ray film. The Flash Scan is available from DPIX, a Xerox company, whose capabilities of the flash scanner are incorporated herein by reference and their entirety. The Flash Scan is used to replace x-ray film and it is placed behind a scintillator screen. As x-rays from an x-ray source of the present invention impact the scintillator screen, photons are emitted from the scintillator screen. These photons are then captured by the amorphous silicone sensor array of the Flash Scan screen. The Flash Scan 30 screen has a resolution of 127 microns and measures 12 inches by 16 inches. This screen size allows the capturing of large images without the need to mosaic, that is, pasting images together. The key characteristic of the Flash Scan 30 screen is that it can record information in real time. These images can be electronically stored in the storage of the portable computer.

Using the portable x-ray source, three different views of the object being tested are captured by the Flash Scan screen and stored in the storage of the portable computer system. These images are then used to construct a three-dimensional image of the object being tested. The three-dimensional image is then exported into the Pro-Engineer coordinate system, which then allows the CT image to be overlaid onto the drawing of the part being inspected.

DETAILED DESCRIPTION OF THE INVENTION

Figure 1:
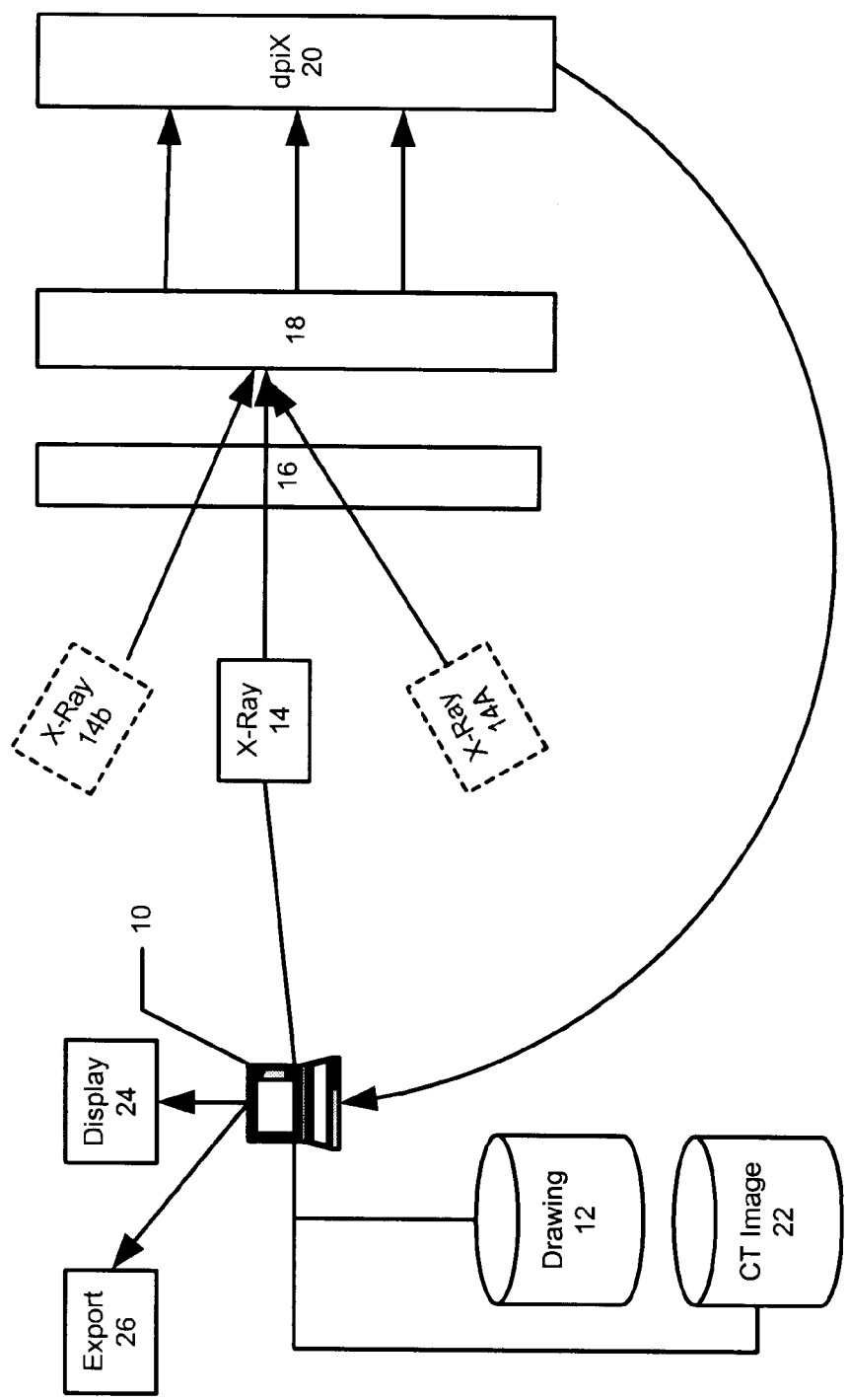
FIG. 1 illustrates the overall system architecture according to one embodiment of the present invention.

As noted above the present invention is a system and method for portable NDE with real time three-dimensional tomography capabilities. Referring to FIG. 1, the overall architecture of the present invention is illustrated. Computer 10 is a portable computer, which may be a laptop computer, small personal computer, or other specialized computing system comprising memory, storage, stored programs, and communication capability. Computer 10 is connected to x-ray source 14. Computer 10 provides instructions to x-ray source 14 to emit x-rays for imaging purposes. X-ray source 14 creates multiple views by exposing the object being analyzed 16 from different angles. Thus x-ray source 14 and position 14a (shown in phantom) illuminates object 16 from a different angle as does x-ray source 14 at location 14b (shown in phantom) which also illuminates object 16 from yet another angle.

With each illumination x-rays pass through object 16 onto a scintillator 18. Scintillator 18 receives the x-rays from the various illumination angles. As x-rays hit the scintillator screen 18 they cause photons to be emitted. These emitted photons are then captured by an amorphous silicone sensor array 20. Such array may be found in the Flash Scan 30 available from DPIX, a Xerox company, whose capabilities are incorporated in area and by reference in their entirety. The images are captured by the Flash Scan screen 20 and are electronically communicated back to computer 10. Thus in rapid sequence, the Flash Scan screen 20 receives multiple images from the x-ray source 14 and transmits them back to the computer 10 for subsequent processing.

Computer 10 also comprises algorithms for assembling the various views from the x-ray source 14 into a three-dimensional CT image of the objects 16 being examined. These images are stored in a separate image database 22 within the appropriate identifier associated with the part being examined.

Thereafter, computer 10 which further comprises the Pro-Engineer software superimposes the three-dimensional image stored in the image database 22 over the CAD/CAM drawing for the part being examined from the drawing database 12 computer 10 further comprises algorithms that allows manipulation of the various images to superimpose them and combine the images in the coordinate space of the Pro-Engineer program. Thereafter the superimposed three-dimensional image and part drawing are displayed on display 24 for ultimate examination and determination of defects by an appropriately trained analyst. Alternatively, the combined record can be stored or exported for subsequent analysis and storage. Using appropriate communications software for export 26.

Thus the system of the present invention allows engineering and design support via portable NDE to be realized. The portable system incorporates three-dimensional CT forming algorithims and integration into the pro-engineer coordinate system. It should be noted that while certain specific systems have been recited, these are not meant as limitations. For example a system having equivalent or better capabilities to the Flash Scan system would be appropriate for the present invention, as would the wide variety of computer systems. Further, while the Pro-Engineer CAD/CAM system has been mentioned, other CAD/CAM systems will also find suitable use for the present invention.

Using the present invention a variety of NDE can be performed. For example weld inspections may be accomplished for complex welds. Casting inspections may also be performed for both solid casting and investment castings with complex internal passageways. Such castings may be of aluminum or cast-iron and may be examined for typical porosity and inclusions. Once such examination of castings is made, the computer system of the present invention can create various cuts in various planes to measure internal passages. Computer generated dimensions can then be compared to the actual measurements.

Inspection of composite structures may be conducted. Honeycomb laminates or solid laminates may be tested with the portable system including most made from fiberglass, graphite epoxy, Teflon, and aluminum.

Pipe inspections may also be performed which are critical in such areas as oil and gas pipelines and alike. Defects such as cracks, corrosion, and abrasive wire may all be evaluated using the present invention.

The system and method for non-destructive examination has now been illustrated. It will be apparent to this skilled in the art but other variations of the present invention are possible without deporting from the scope of the invention as disclosed.

We claim:

1. A system for portable non-destructive examination comprising:

a portable processor comprising CAD/CAM program, the CAD/CAM program rendering drawings in an associated coordinate space, the processor further comprising instructions for creating three dimensional images from a plurality of x-ray images;

an x-ray source for creating x-rays connected to the processor for irradiating a target;

a scintillator screen for receiving the x-rays that pass through the target and for generating photons;

a silicon sensor array connected to the processor for receiving the photons, for generating a x-ray images of the target, and for transmitting the x-ray images of the target to the processor; and the processor further comprising instructions rendering the three dimensional image into the coordinate system of the CAD/CAM program.

2. The apparatus of claim 1 further comprising a database comprising at least a CAD/CAM image the target; and the processor further comprising instructions for superimposing the three dimensional x-ray image of the target onto the CAD/CAM image of the target.

3. A method for Non-destructive examination of a target comprising:

irradiating a target with a portable x-ray source from a plurality of angles to create a plurality of x-ray images;

receiving the x-rays that pass through the target by a scintillator screen;

the scintillator screen producing photons;

receiving the photons by a silicon sensor array;

rendering a plurality of x-ray image by the silicon sensor array;

the silicon sensor array transmitting the plurality of x-ray images to a processor; and, the processor rendering a three dimensional image from the plurality of silicon sensor array x-ray images and translating the three dimensional image into a coordinate systems of a CAD/CAM program.

4. The method for non-destructive examination of a target of claim 3 further comprising;

superimposing the three dimensional x-ray image onto a CAD/CAM image of the target from a database of targets associated with the processor.

* * * * *